US 6,651,513 B2

(12) United States Patent
Wenger et al.

(10) Patent No.: US 6,651,513 B2
(45) Date of Patent: Nov. 25, 2003

(54) VIBRATION METER AND METHOD OF MEASURING A VISCOSITY OF A FLUID

(75) Inventors: Alfred Wenger, Neftenbach (CH); Michael Fuchs, Eschbach (DE); Christian Matt, Aesch (CH); Wolfgang Drahm, Freising (DE)

(73) Assignee: Endress + Hauser Flowtec AG, Reinach (CH)

( * ) Notice: Subject to any disclaimer, the term of this patent is extended or adjusted under 35 U.S.C. 154(b) by 74 days.

(21) Appl. No.: 09/844,013

(22) Filed: Apr. 27, 2001

(65) Prior Publication Data

US 2001/0039829 A1 Nov. 15, 2001

Related U.S. Application Data (60) Provisional application No. 60/221,622, filed on Jul. 28, 2000.

(30) Foreign Application Priority Data

Apr. 27, 2000 (DE) .......................................... 100 20 606
May 12, 2000 (EP) ............................................. 00110086

(51) Int. Cl.⁷ .............................. G01N 11/10; G01F 1/84
(52) U.S. Cl. .............................. 73/861.357; 73/861.356; 73/54.24
(58) Field of Search ............................. 73/54.24, 54.25, 73/54.26, 54.27, 54.41, 861.354, 861.356, 861.355, 861.357

(56) References Cited

U.S. PATENT DOCUMENTS

| 4,187,721 | A |   | 2/1980  | Smith            |            |
|-----------|---|---|---------|------------------|------------|
| 4,524,610 | A |   | 6/1985  | Fitzgerald et al.|            |
| 4,801,897 | A |   | 1/1989  | Flecken          |            |
| 4,840,071 | A |   | 6/1989  | Lew              |            |
| 4,876,879 | A |   | 10/1989 | Ruesch           |            |
| 5,253,533 | A |   | 10/1993 | Lam et al.       |            |
| 5,301,557 | A |   | 4/1994  | Cage et al.      |            |
| 5,357,811 | A |   | 10/1994 | Hoang            |            |
| 5,359,881 | A |   | 11/1994 | Kalotay et al.   |            |
| 5,531,126 | A | * | 7/1996  | Drahm            | 73/861.356 |
| 5,549,009 | A | * | 8/1996  | Zaschel          | 73/861.355 |

(List continued on next page.)

FOREIGN PATENT DOCUMENTS

| DE | 412 4296     | 2/1992  |
|----|--------------|---------|
| EP | 0 272 758    | 6/1988  |
| EP | 0 631 662    | 10/1997 |
| EP | 0 849 568    | 6/1998  |
| EP | 0 866 319    | 9/1998  |
| EP | 0 867 694    | 9/1998  |
| WO | WO 93/19348  | 9/1993  |
| WO | WO 94/14047  | 6/1994  |
| WO | WO 95/16897  | 6/1995  |

OTHER PUBLICATIONS

Wenger, A. P., *Vibrating Fluid Densimeters: A Solution to the Viscosity Problem*, Aug. 3, 1980, "IEEE Transactions on Industrial Electronics and Control Instrumentation", vol. IECI–27, No. 3, pp. 247–253.

Primary Examiner—Edward Lefkowitz
Assistant Examiner—Michael Cygan
(74) Attorney, Agent, or Firm—Bose McKinney & Evans LLP (57) ABSTRACT

A vibration meter and a method of measuring a viscosity of a fluid flowing through a pipe are disclosed. The vibration meter comprises meter electronics and a transducer assembly with an electromechanical excitation arrangement and with a flow tube which oscillates in operation. A sensor arrangement produces sensor signals representative of inlet-side and outlet-side deflections of the flow tube. An evaluation circuit derives from said sensor signals and from an excitation current generated by an excitation circuit for the excitation arrangement a viscosity value representative of the viscosity of the fluid.

12 Claims, 6 Drawing Sheets

U.S. PATENT DOCUMENTS

| | | |
|---|---|---|
| 5,557,973 A | 9/1996 | Koudal et al. |
| 5,648,616 A | 7/1997 | Keel |
| 5,661,232 A | 8/1997 | Van Cleve et al. |
| 5,687,100 A | 11/1997 | Buttler et al. |
| 5,737,745 A * | 4/1998 | Matsumoto et al. ........ 711/114 |
| 5,796,011 A | 8/1998 | Keita et al. |
| 6,006,609 A | 12/1999 | Drahm et al. |
| 6,330,832 B1 * | 12/2001 | Normen et al. ........ 73/861.354 |

* cited by examiner

VIBRATION METER AND METHOD OF MEASURING A VISCOSITY OF A FLUID

RELATED APPLICATIONS

This application claims the benefit of U.S. Provisional Application No. 60/221,622, filed Jul. 28, 2000, and claims priority to German Application No. 100 20 606.9, filed Apr. 27, 2000, and European Patent Office Application No. 00110086.6.

FIELD OF THE INVENTION

This invention relates to a method of measuring a viscosity of a fluid flowing through a pipe, and to a vibration meter for carrying out this method. Furthermore, the invention relates to the use of a flexural mode Coriolis mass flowmeter-densimeter for measuring the viscosity of the fluid.

BACKGROUND OF THE INVENTION

Coriolis mass flowmeter-densimeters are preferably used for measuring a mass flow rate and/or a density of a fluid flowing through a pipe with a high degree of accuracy.

A flexural mode Coriolis mass flowmeter-densimeter, as is well known, is a vibration meter that has at least one fluid-conducting flow tube which is inserted into a pipe in a fluid-tight manner, particularly in a pressure-tight manner, and which during operation oscillates multimodally, particularly bimodally, about a position of rest at at least one frequency. By means of an electromechanical excitation arrangement, the flow tube is commonly excited in a first, flexural mode of vibration such that Coriolis forces are produced in the moving fluid. In the case of a straight flow tube, the first, flexural mode may, for instance, be a fundamental mode of an elastic beam clamped at both ends, which, as is well known, has a single antinode. In the case of a bent flow tube, particularly a U- or Ω-shaped tube, a fundamental mode of a beam clamped at one end is usually excited as the first, flexural mode.

In such vibration meters, the Coriolis forces caused in the moving fluid by the first, flexural mode simultaneously excite a second vibration mode, whose amplitude is also dependent on mass flow rate.

To determine the mass flow rate, a vibration of the flow tube at an inlet end and a vibration of the flow tube at an outlet end are sensed by means of a suitable sensor arrangement and converted into a first sensor signal, representing the inlet-side vibrations, and a second sensor signal, representing the outlet-side vibrations.

Since the second vibration mode, here also a flexural mode, is superimposed on the first flexural mode, the two vibrations differ in phase. In Coriolis mass flowmeter-densimeters, this phase difference, which is also measurable between the two sensor signals in a corresponding manner, serves as a measurand representative of mass flow rate.

In Coriolis mass flowmeter-densimeters, a resonance frequency and/or the amplitude of the first, flexural mode are generally measurably dependent on the density of the fluid. Thus, if the flow tube is constantly excited at the resonance frequency of the first, flexural mode, for example, this resonance frequency is a measure of the instantaneous density of the fluid.

Vibration meters of the kind described, particularly Coriolis mass flowmeter-densimeters, have been known for a long time. For example, U.S. Pat. Nos. 4,187,721, 4,801,897, 4,876,879, 5,301,557, 5,357,811, 5,557,973, 5,648,616, 5,687,100, 5,796,011, and 6,006,609 as well as European Patent 866 319 each disclose a vibration meter for measuring a mass flow rate and a density of a fluid flowing through a pipe, which vibration meter comprises:

a transducer assembly
  with at least one flow tube inserted into the pipe,
    which is clamped at an inlet end and an outlet end so as to be capable of vibratory motion, and
    which in operation oscillates relative to a position of rest at an adjustable excitation frequency,
  with an electromechanical excitation arrangement for simultaneously producing spatial deflections and elastic deformations of the flow tube, and
  with a sensor arrangement, responsive to lateral deflections of the flow tube,
    for generating a first sensor signal, representative of an inlet-side deflection of the flow tube, and
    for generating a second sensor signal, representative of an outlet-side deflection of the flow tube; and
meter electronics
  with an excitation circuit which generates an excitation current for feeding the excitation arrangement, and
  with an evaluating circuit which derives from the first and second sensor signals a mass flow rate value representative of the mass flow rate of the fluid and a density value representative of the density of the fluid.

Another physical parameter that is important for describing a moving fluid is viscosity. One can distinguish between kinematic viscosity and dynamic viscosity.

Viscometers and density-measuring vibration meters for moving fluids are also known in the art. U.S. Pat. No. 4,524,610, for example, discloses a vibration meter for measuring a viscosity of a fluid flowing through a pipe, which vibration meter comprises:

a transducer assembly
  with a straight flow tube inserted into the pipe which
    has a lumen conducting the fluid and
    is clamped at an inlet end and an outlet end so as to be capable of vibratory motion,
  with an electromechanical excitation arrangement for producing lateral deflections and/or torsional vibrations of the flow tube, and
  with a sensor arrangement, responsive to torsional vibrations of the flow tube, for generating a sensor signal representative of central torsions of the flow tube; and
meter electronics
  with an excitation circuit which generates an excitation current feeding the excitation arrangement, and
  with an evaluating circuit
    which derives from the sensor signal and the excitation current a viscosity value representative of the viscosity of the fluid.

In this vibration meter serving as a viscometer-densimeter, the flow tube oscillates either alternately in the above-mentioned first, flexural mode for determining density or in a torsional mode for determining viscosity, or in both modes simultaneously, but at different frequencies. The torsional vibrations performed by the flow tube cause shearing forces in the fluid, which, in turn, have a damping effect on the torsional vibrations.

WO-A 95/16897 discloses a radial mode vibration meter serving as a Coriolis mass flowmeter-densimeter-viscometer for measuring a viscosity of a fluid flowing through a pipe, which vibration meter comprises:

a transducer assembly
  with a straight flow tube inserted into the pipe, which flow tube has a lumen conducting the fluid and is clamped at an inlet end and an outlet end so as to be capable of vibratory motion, with an electromechanical excitation arrangement for producing axisymmetric deformations and/or lateral deflections of the flow tube, and with a sensor arrangement, responsive to axisymmetric deformations of the flow tube, for producing a sensor signal representative of the deformations of the flow tube; and meter electronics with an excitation circuit which generates an excitation current feeding the excitation arrangement, and with an evaluating circuit which derives from the sensor signal and the excitation current a viscosity value representative of the viscosity of the fluid.

In this Coriolis mass flowmeter-densimeter-viscometer, the flow tube for determining viscosity and mass flow rate oscillates primarily in an axisymmetric radial mode, i.e., in a mode in which the wall of the flow tube is elastically deformed in such a way that an axis of gravity of the flow tube remains essentially in a static position of rest. In addition, the flow tube is exited, at least temporarily, in a secondary mode for instance in the before mentioned first, flexural mode, which serves to determine the density and pressure of the fluid.

While WO-A 95/16897 describes that radial mode vibration meters can be used to measure both the mass flow rate and the viscosity of fluids, the use of such vibration meters for mass flow rate measurements has so far been limited nearly exclusively to gaseous fluids. It has turned out that the damping effect of viscosity, particularly on the amplitude of the above-mentioned, preferably mass-flow-rate-dependent second vibration mode, is so high that even at viscosities that are just slightly above that of water, this second vibration mode is practically no longer detectable with sensors.

U.S. Pat. No. 5,359,881 discloses a method of measuring the viscosity of a moving fluid which uses a flexural mode Coriolis mass flowmeter-densimeter to determine mass flow rate and in which a pressure difference in the moving fluid along the direction of flow is additionally sensed to determine the viscosity of the fluid.

Furthermore, U.S. Pat. Nos. 5,253,533 and 6,006,609 disclose flexural mode Coriolis mass flow/density sensors which, in addition to sensing mass flow rate and/or density, are suited for determining the viscosity of a fluid. These Coriolis mass flow/density sensors each have a straight flow tube which in operation oscillates, simultaneously with a first, flexural mode, in a torsional mode and thereby performs, at least in sections, torsional vibrations about a longitudinal axis of the flow tube.

It has turned out that the viscosities hitherto determined in such Coriolis mass flow meters by measuring solely the excitation current practically only for the purpose of compensating the primary measured values, namely a mass flow rate value and a density value, are too inaccurate to be suitable for output as additional viscosity values.

SUMMARY OF THE INVENTION

It is therefore an object of the invention to provide a vibration meter for accurately measuring a viscosity of a fluid flowing through a pipe which is also suited for measuring, particularly simultaneously, a mass flow rate and a density of the fluid. The invention further provides a method which serves to increase the accuracy of viscosity measurements by means of Coriolis mass flowmeter-densimeters.

To attain the object, the invention provides a vibration meter for measuring a viscosity of a fluid flowing through a pipe, which vibration meter comprises:

a transducer assembly with at least one flow tube inserted into the pipe which has a lumen conducting the fluid and is clamped at an inlet end and an outlet end so as to be capable of vibratory motion, with an electromechanical excitation arrangement for producing spatial deflections of the flow tube, and with a sensor arrangement, responsive to lateral deflections of the flow tube, for generating a first sensor signal, representative of an inlet-side deflection of the flow tube, and for generating a second sensor signal, representative of an outlet-side deflection of the flow tube, the flow tube oscillating in operation relative to a position of rest at an adjustable excitation frequency to produce viscous friction in the fluid; and meter electronics with an excitation circuit which generates an excitation current feeding the excitation arrangement, and with an evaluating circuit which derives from the first sensor signal and/or the second sensor signal and from the excitation current a viscosity value representative of the viscosity of the fluid.

The invention also provides a method of measuring a viscosity of a fluid flowing through a pipe using a vibration meter comprising:

a transducer assembly with at least one flow tube inserted into the pipe which in operation oscillates relative to a position of rest at an adjustable excitation frequency, with an electromechanical excitation arrangement for producing spatial deflections of the flow tube, and with a sensor arrangement, responsive to lateral deflections of the flow tube, for sensing an inlet-side and an outlet-side deflection of the flow tube; and meter electronics with an excitation circuit which generates an excitation current feeding the excitation arrangement, and an evaluating circuit, the vibration meter providing a density value, representative of a density of the fluid, and an excitation frequency value, representative of the excitation frequency, said method comprising the steps of:

generating vibrations of the flow tube at the excitation frequency to produce viscous friction in the fluid;

sensing the excitation current feeding the excitation arrangement to generate a friction value representative of the viscous friction;

sensing an inlet-side and/or an outlet-side deflection of the flow tube to generate an estimate representative of a velocity of a motion of the fluid, which causes the viscous friction;

dividing the friction value by the estimate to obtain a quotient value representative of a damping of the oscillating flow tube caused by the viscous friction;

deriving from the density value and the excitation frequency value a correction value dependent on the density of the fluid and on the excitation frequency; and deriving from the quotient value and the correction value a viscosity value representative of the viscosity of the fluid.

In a first preferred embodiment of the vibration meter of the invention, the evaluating circuit generates from the first sensor signal and/or the second sensor signal an estimate of a velocity of a motion of the fluid, which causes viscous friction.

In a second preferred embodiment of the vibration meter of the invention, the evaluating circuit derives from the excitation current a friction value representative of the viscous friction in the fluid.

In a third preferred embodiment of the vibration meter of the invention, the evaluating circuit derives from the friction value and the estimate a quotient value representative of a damping of the oscillating flow tube caused by the viscous friction.

In a fourth preferred embodiment of the vibration meter of the invention, elastic deformations of the lumen of the flow tube are caused by the spatial deflections of the flow tube.

In a fifth preferred embodiment of the vibration meter of the invention, torsions are caused in the flow tube about a longitudinal axis by the spatial deflections of the flow tube.

In a sixth preferred embodiment of the invention, the vibration meter delivers a mass flow rate value representative of an instantaneous mass flow rate of the fluid.

In a seventh preferred embodiment of the invention, the vibration meter delivers a density value representative of an instantaneous density of the fluid.

In a first preferred embodiment of the method of the invention, the viscosity value is obtained by dividing the quotient value by the correction value.

In a second preferred embodiment of the method of the invention, the viscosity value is obtained by squaring the quotient value.

An aspect of the invention is to derive the viscosity from the measured excitation current and from a lateral deflection of the flow tube which is continuously sensed during operation of vibration meters of the kind described, particularly of Coriolis mass flowmeter-densimeters, preferably from the vibrations sensed at the inlet end and/or outlet end to measure mass flow rate.

One advantage of the invention is that it can be implemented using conventional flexural mode Coriolis mass flow/density sensors of the kind described without having to make any changes to the mechanical design of such sensors. Thus, the method of the invention can also be implemented in Coriolis mass flowmeter-densimeters that are already in use.

BRIEF DESCRIPTION OF THE DRAWINGS

The invention and further advantages will become more apparent by reference to the following description of embodiments taken in conjunction with the accompanying drawings, in which.

DETAILED DESCRIPTION OF EXEMPLARY EMBODIMENTS

While the invention is susceptible to various modifications and alternative forms, exemplary embodiments thereof have been shown by way of example in the drawings and will herein be described in detail. It should be understood, however, that there is no intent to limit the invention to the the particular forms diclosed, but on the contrary, the intention is to cover all modifications, equivalents, and alternatives falling within the spirit and scope of the invention as defined by the intended claims.

Figure 1:
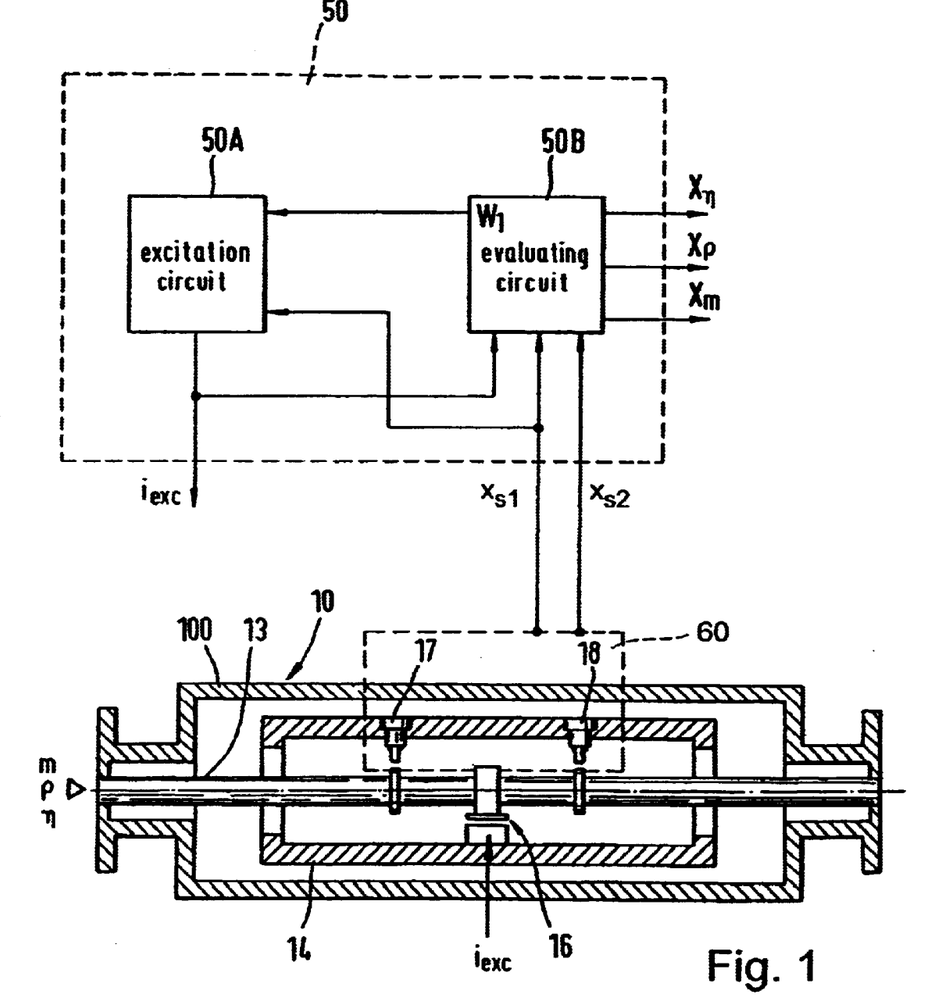
FIG. 1 shows schematically a vibration meter for a moving fluid.

FIG. 1 shows schematically a vibration meter that serves to sense a viscosity $\eta$ of a fluid flowing through a pipe (not shown) and to map it into a viscosity value $X_\eta$ representative of the viscosity $\eta$ of the fluid.

Furthermore, the vibration meter, besides determining the viscosity $\eta$, preferably serves to determine a density $\rho$ and a mass flow rate m of the fluid, particularly simultaneously, and to convert them in a corresponding manner into a density value $X_\rho$, representing the density $\rho$, and a mass flow rate value $X_m$, representing the mass flow rate m.

To accomplish this, the vibration meter is preferably designed as a Coriolis mass flowmeter-densimeter. The construction and use of such Coriolis mass flowmeter-densimeters for measuring the mass flow rate m and/or the density $\rho$ are described, for example, in the above-mentioned U.S. Pat. Nos. 4,187,721, 4,876,879, 5,648,616, 5,687,100, and 5,796,011 as well as in European Patent 866 319, the disclosures of which are hereby incorporated by reference.

To sense the above-mentioned parameters describing the fluid, namely the viscosity $\eta$, the density $\rho$, and the mass flow rate m, the vibration meter comprises a transducer assembly 10, which is inserted into the pipe in a fluid-tight manner, particularly in a pressure-tight manner.

The vibration meter further comprises meter electronics 50 for controlling transducer assembly 10 and for generating the aforementioned measured values. If the vibration meter is designed to be coupled to a field bus, particularly to a serial field bus, meter electronics 50 will include a suitable communication interface for data communication, e.g., for the transmission of the measured values to a higher-level stored-program control or a higher-level process control system. Meter electronics 50 may, of course, be housed in a suitable electronics case (not shown) in the manner familiar to those skilled in the art.

Figure 2:
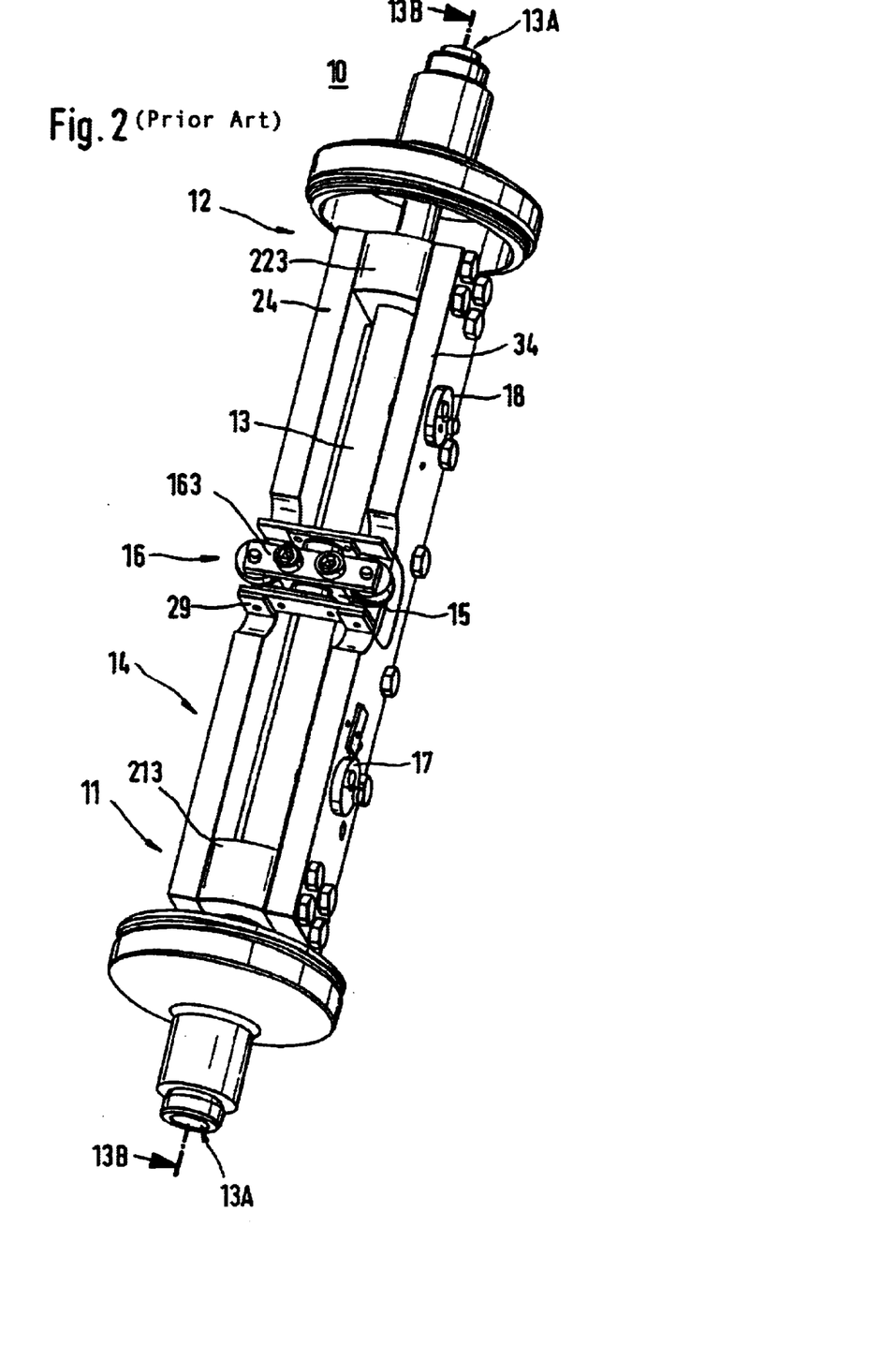
FIG. 2 is a first perspective view of an embodiment of a transducer assembly of the vibration meter of FIG. 1.
Figure 3:
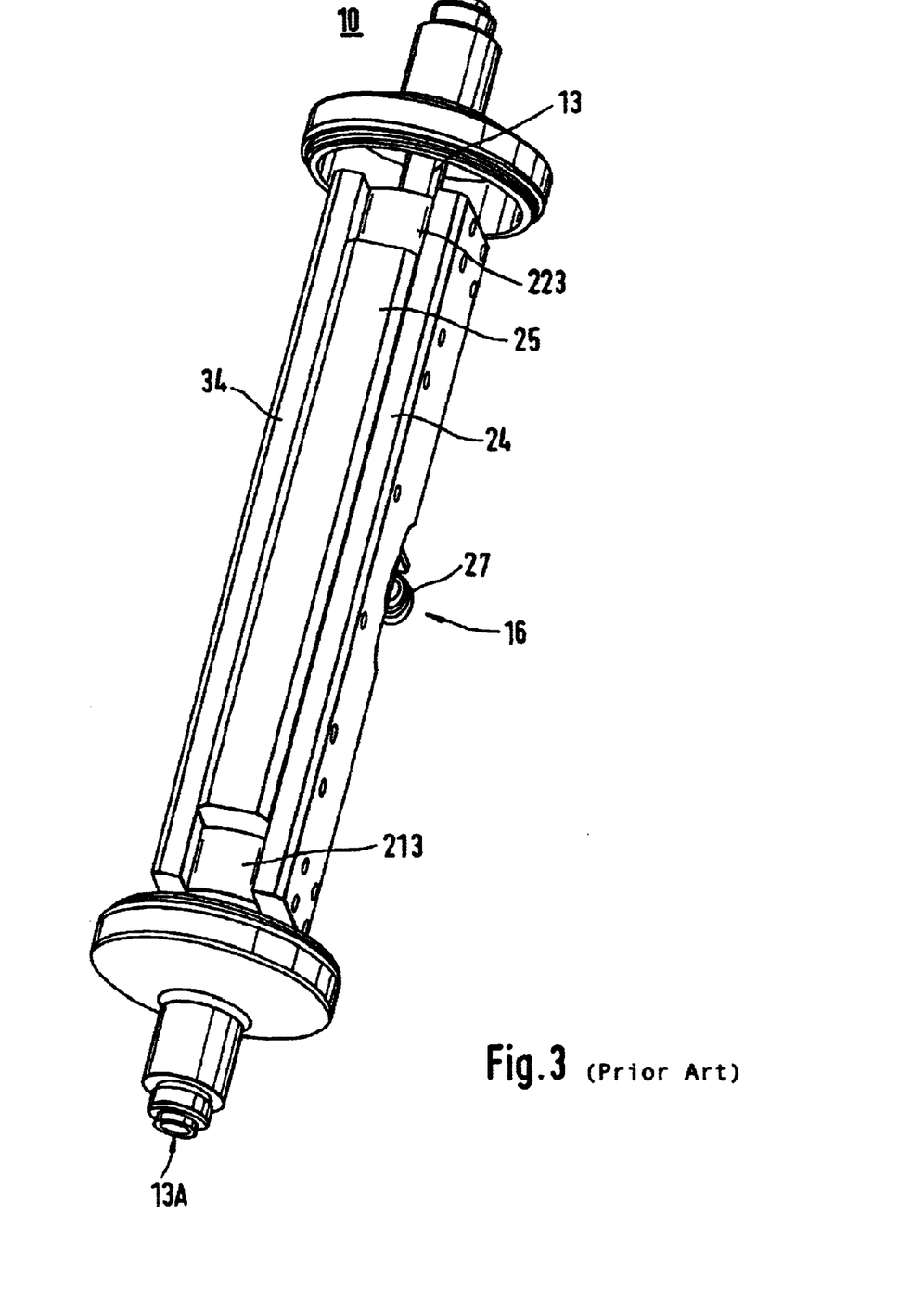
FIG. 3 is a second perspective view of the transducer assembly of FIG. 2.

FIGS. 2 and 3 show an embodiment of a physical-to-electrical converter arrangement serving as transducer assembly 10. For example, the design of such a transducer assembly is also described in detail in U.S. Pat. No. 6,006,609, the disclosures of which are hereby incorporated by reference. Such a transducer assembly is used, for example, in Coriolis mass flowmeter-densimeters of the "PROMASS I" series, which are manufactured by the applicant.

Transducer assembly 10 comprises a straight flow tube 13, which has an inlet end 11, an outlet end 12, a predeterminable, elastically deformable lumen 13A, and a predeterminable nominal diameter, as well as a rigid support frame 14, which is enclosed by a housing 100 and in which flow tube 13 is clamped so as to be capable of vibratory motion. "Elastic deformation" of lumen 13A as used herein means that in order to produce reaction forces describing the fluid, namely Coriolis forces, mass inertial forces, and/or shearing forces, during operation of transducer assembly 10, a three-dimensional shape and/or a spatial position of the fluid-conducting lumen 13A are changed in a predeterminable cyclic manner, particularly periodically, within an elasticity range of flow tube 13, cf., for example, U.S. Pat. Nos. 4,801,897, 5,648,616, 5,796,011, and/or 6,006,609, the disclosures of which are hereby incorporated by reference. Materials especially suited for flow tube 13 are titanium alloys, for example. It is also possible to use other materials commonly employed for such flow tubes, particularly for bent tubes, such as stainless steel or zirconium.

Support frame 14 is fixed at inlet end 11 to an inlet plate 213 surrounding flow tube 13, and at outlet end 12 to an outlet plate 223 surrounding flow tube 13. Support frame 14 has a first support plate 24 and a second support plate 34, which are fixed to inlet plate 213 and outlet plate 223 in such a way as to be disposed in essentially parallel relationship to flow tube 13 and in spaced relationship from the latter and from each other, see FIG. 2. Thus, facing side surfaces of the two support plates 24, 34 are also parallel to each other.

Secured to flow tube 13 in spaced relation from support plates 24, 34 is a longitudinal bar 25, which serves as a balancing mass for absorbing vibrations of flow tube 13. As shown in FIG. 3, longitudinal bar 25 extends virtually parallel to the entire oscillable length of flow tube 13.

This, however, is not mandatory; longitudinal bar 25 may, of course, be shorter if necessary.

Support frame 14 with the two support plates 24, 34, inlet plate 213, outlet plate 223, and, optionally, longitudinal bar 25 thus has a longitudinal axis of gravity which is parallel to a longitudinal axis 13B of flow tube 13.

In FIGS. 2 and 3, it is indicated by the heads of the screws shown that the above-mentioned fixing of support plates 24, 34 to inlet plate 213 and outlet plate 223 and to longitudinal bar 25 may be done by screwing; it is also possible to use other suitable forms of fastening familiar to those skilled in the art.

As shown in FIG. 2, transducer assembly 10 further comprises an electromechanical excitation arrangement 16, which serves to spatially deflect flow tube 13 from a static position of rest during operation, and thus to elastically deform the flow tube in a predeterminable manner.

Figure 4:
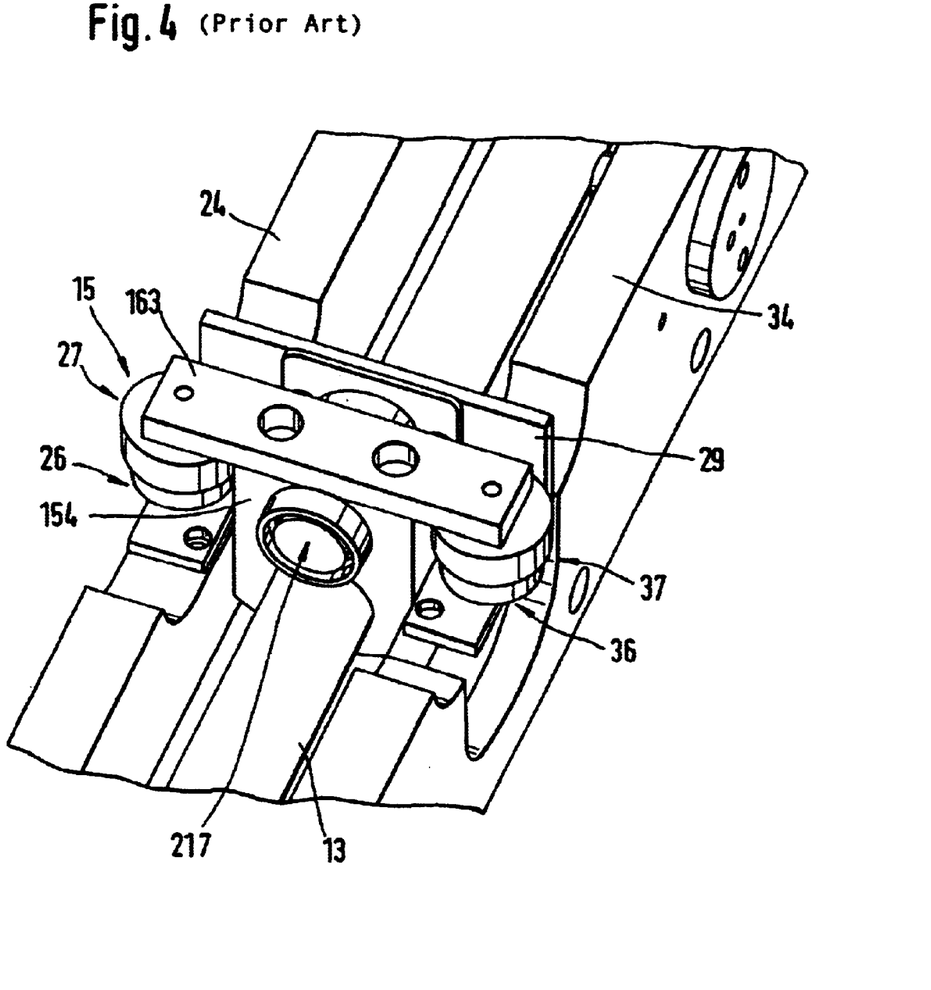
FIG. 4 is a perspective view of an enlarged portion of the transducer assembly of FIG. 2.

To accomplish this, excitation arrangement 16, as shown in FIG. 4, has a rigid lever arrangement 15, here a T-shaped arrangement, with a cantilever 154 and a yoke 163, the cantilever being rigidly fixed to flow tube 13. Yoke 163 is rigidly fixed to an end of cantilever 154 remote from flow tube 13, such that it is transverse to longitudinal axis 13B of flow tube 13. Cantilever 154 may, for instance, be a metal disk which receives the flow tube in a bore. For further suitable implementations of lever arrangement 15, reference is made to the above-mentioned U.S. Pat. No. 6,006,609.

Lever arrangement 15, as is readily apparent from FIG. 2, is preferably arranged to act on flow tube 13 approximately midway between inlet end 11 and outlet end 12, so that in operation, flow tube 13 will exhibit a maximum lateral deflection at a centric point.

To drive the lever arrangement 15, excitation arrangement 16, as shown in FIG. 4, comprises a first excitation coil 26 and an associated first permanent magnet 27 as well as a second excitation coil 36 and an associated second permanent magnet 37, which two excitation coils 26, 36 are joined, preferably nonpermanently, to support frame 14 below yoke 163 on both sides of flow tube 13. The two excitation coils 26, 36 are preferably connected in series; if necessary, they may, of course, be connected in parallel.

As shown in FIGS. 2 and 4, the two permanent magnets 27, 37 are fixed to yoke 163 at such a distance from each other that during operation of transducer assembly 10, permanent magnets 27 and 26 will be permeated essentially by magnetic fields of excitation coils 26 and 36, respectively, and moved by corresponding electromagnetic forces. To this end, excitation arrangement 16 is fed by a likewise oscillating, unipolar or bipolar excitation current $i_{exc}$ of adjustable amplitude and adjustable frequency $f_{exc}$ from a suitable excitation circuit 50A of meter electronics 50, such that in operation, excitation coils 26, 36 are traversed by this current, so that the magnetic fields for moving permanent magnets 27, 37 are produced. Excitation current $i_{exc}$ may, for example, be a harmonic, a triangular wave, or a square wave. The, preferably single, frequency $f_{exc}$ of excitation current $i_{exc}$, as is customary in vibration meters of the kind described, corresponds to an instantaneous mechanical resonance frequency of the fluid-carrying flow tube 13.

The motions of permanent magnets 27, 37 produced by the magnetic fields of excitation coils 26, 36 are transmitted via yoke 163 and cantilever 154 to flow tube 13. These motions of permanent magnets 27, 37 are such that yoke 163 is deflected from its position of rest at the excitation frequency $f_{exc}$, alternately in the direction of support plate 24 and in the direction of support plate 34. A corresponding axis of rotation of lever arrangement 15, which is parallel to the above-mentioned longitudinal axis 13B of flow tube 13, may pass through cantilever 154, for example.

Preferably, support frame 14 further comprises a holder 29 for electromagnetic excitation arrangement 16. This holder 29 is connected, preferably nonpermanently, with support plates 24, 34, and serves in particular to hold excitation coils 26, 36 and individual components of the below-mentioned magnetic-bearing arrangement 217.

As mentioned, excitation arrangement 16 serves to excite flow tube 13 into mechanical vibration about a static position of rest, whereby the tube performs at least lateral deflections, particularly laterally oscillating deflections.

In the transducer assembly 10 of the embodiment, these lateral deflections simultaneously cause an elastic deformation of the lumen 13A of flow tube 13, which is firmly clamped at inlet end 11 and outlet end 12 in the manner described above. This deformation of the lumen 13A of flow tube 13 extends over virtually the entire length of flow tube 13.

Furthermore, due to the clamping of flow tube 13 and to a torque acting on flow tube 13 via lever arrangement 15, torsion is induced in flow tube 13, at least in sections thereof, simultaneously with the lateral deflection. This torsion of flow tube 13 may be such that the direction of a lateral deflection of the end of the cantilever remote from flow tube 13 is either the same as or opposite to that of the lateral deflection of flow tube 13. In other words, flow tube 13 can perform torsional vibrations in a first torsional mode, corresponding to the former case, or in a second torsional mode, corresponding to the latter case. In the transducer assembly 10 of the embodiment, a natural frequency of the second torsional mode, e.g., 900 Hz, is approximately twice as high as that of the first torsional mode.

If flow tube 13 is to perform torsional vibrations only in the second torsional mode, excitation arrangement 16 will advantageously incorporate a magnetic-bearing arrangement 217 based on the eddy-current principle, which serves to adjust and/or stabilize the position of the axis of rotation, which depends particularly on the instantaneous density of the fluid. With the magnetic-bearing arrangement 217 it can thus be ensured that flow tube 13 always vibrates in the second torsional mode, so that any external interfering effects on flow tube 13 will not result in a spontaneous change to another torsional mode, particularly to the first torsional mode. Details of such a magnetic-bearing arrangement are described, for example, in U.S. Pat. No. 6,006,609; the use of such magnetic-bearing arrangements is also known from transducers of the aforementioned "PROMASS I" series.

For the transducer assembly 10 of the embodiment, the excitation frequency $f_{exc}$ will preferably be adjusted so that exclusively the second torsional mode will be excited and, accordingly, the first torsional mode will be substantially suppressed; if necessary, however, the first torsional mode may be excited.

As shown in FIG. 1, transducer assembly 10 further comprises a sensor arrangement 60, which serves to sense instantaneous spatial deflections of flow tube 13 and generate corresponding signals, particularly analog signals. To accomplish this, sensor arrangement 60 comprises a first sensor 17, which is responsive to inlet-side, first laterally oscillating deflections of flow tube 13, and a second sensor 18, which is responsive to outlet-side, second laterally oscillating deflections of flow tube 13. As shown in FIG. 2, the two sensors 17, 18 are positioned along flow tube 13 at a given distance from each other, particularly at the same distance from the midpoint of flow tube 13, by being fixed to support frame 14, particularly to one of support plates 24, 34.

For sensors 17, 18, velocity-measuring electrodynamic sensors are preferably used. It is also possible to use displacement- or acceleration-measuring electrodynamic or optical sensors, or other sensors familiar to those skilled in the art that are responsive to such deflections.

Thus, in operation, the two sensors 17, 18 of sensor arrangement 60 generate a first sensor signal $x_{s1}$, representative of the inlet-side lateral deflections, and a second sensor signal $x_{s2}$, representative of the outlet-side lateral deflections.

As shown in FIG. 1, sensor signals $x_{s1}$, $x_{s2}$ are applied to a preferably programmable evaluating circuit 50B of meter electronics 50, which serves to generate the viscosity value $X_\eta$ and the density value $X_\rho$. In a preferred embodiment of the invention, evaluating circuit 50B further provides the mass flow rate value $X_m$.

Each of the two sensor signals $x_{s1}$, $x_{s2}$ has a frequency corresponding to excitation frequency $f_{exc}$.

Preferably, sensor arrangement 60 further comprises an amplifier circuit for adjusting the two sensor signals $x_{s1}$, $x_{s2}$ to the same amplitude. Amplitude control circuits suitable for this purpose are shown in U.S. Pat. No. 5,648,616 or European Patent 866 319, for example.

The excitation frequency $f_{exc}$ is preferably adjusted using a phase-locked loop of excitation circuit 50A, as is usual in such excitation arrangements. For example, the design and use of such a phase-locked loop for adjusting a mechanical resonance frequency are described in detail in U.S. Pat. No. 4,801,897, the disclosers of which are hereby incorporated by reference. It is also possible to use other frequency control circuits familiar to those skilled in the art which serve to adjust mechanical resonance frequencies for vibration meters of the kind described, cf., for example, U.S. Pat. Nos. 4,524,610 and 4,801,897. Regarding the use of such a frequency control circuit for transducers of the kind described, reference is made to the "PROMASS I" series mentioned above.

To adjust the excitation current $i_{exc}$, use is made of an amplifier circuit as is commonly employed in such vibration meters, which is controlled by a frequency control signal representative of the excitation frequency to be adjusted, $f_{exc}$, and by an excitation current control signal representative of the amplitude of the excitation current to be adjusted, $i_{exc}$. The frequency control signal may, for example, be a DC voltage delivered by the above-mentioned frequency control circuit and having an amplitude representative of the excitation frequency $f_{exc}$.

To generate the excitation current $i_{exc}$, excitation circuit 50A comprises a suitable amplitude control circuit which serves to derive the excitation current control signal from the instantaneous amplitude of at least one of the two sensor signals $x_{s1}$, $x_{s2}$, and from a corresponding constant or variable amplitude reference value $W_1$; if necessary, recourse can also be had to an instantaneous amplitude of the excitation current $i_{exc}$ to generate the excitation current control signal. Such amplitude control circuits are also familiar to those skilled in the art. For an example of such an amplitude control circuit, reference is again made to Corolis mass flowmeters of the "PROMASS I" series. The amplitude control circuit of the latter is preferably designed so that in the above-mentioned first, flexural mode, the vibrations of the respective flow tube are maintained at a constant, i.e., density-independent, amplitude value.

The method of determining a viscosity $\eta$ of the fluid in accordance with the invention will now be explained in more detail as applied to the above-described transducer assembly 10. It should be noted that by the term "viscosity", both a dynamic viscosity and a kinematic viscosity of the fluid can be understood, since the two viscosities can be readily converted into one another via the density of the fluid, which is also measured during operation of the vibration meter. Furthermore, instead of the viscosity $\eta$, its reciprocal, i.e., a fluidity of the fluid, can be determined.

In vibration meters with at least one flow tube oscillating in the predetermined manner, the spatial deflections of the respective flow tube cause motions of the fluid, which produce shear forces. These shear forces in the fluid are also determined by the viscosity $\eta$ of the fluid and, in the form of friction losses, have a damping effect on the oscillating flow tube.

It has turned out that a ratio $i_{exc}/\theta$ of the excitation current $i_{exc}$ to a velocity $\theta$ of a shear-forces-inducing motion of the fluid, which velocity is not directly measurable, is a representative estimate of a damping that counteracts this deflection. This damping of the deflection is also determined by a damping component that is due to viscous friction within the fluid, and can thus serve to determine viscosity. Accordingly, to determine the viscosity $\eta$, the velocity $\theta$ of the aforementioned motions of the fluid is determined in addition to the excitation current $i_{exc}$.

For the viscosity-measuring method described in the above-mentioned U.S. Pat. No. 4,524,610, the velocity $\theta$ is estimated of a driving motion performed by a driving lever ("yoke"), which driving motion induces torsion in a corresponding flow tube. This driving lever thus corresponds approximately to lever arrangement 15.

However, lever arrangement 15 is only conditionally suited for measuring the velocity $\theta$ to determine the viscosity of a fluid by a transducer assembly of the kind described; on the one hand, because the position of the axis of rotation of lever arrangement 15, as mentioned, is variable and may therefore be determined on a continuous basis, and, on the other hand, because such a lever arrangement is frequently not provided on transducer assemblies of the kind described, particularly in Coriolis mass flow/density meters.

Therefore, according to the fundamental idea of the invention, the velocity θ is not sensed directly at lever arrangement 15 of transducer assembly 10, but is derived from the sensor signals $x_{s1}$, $x_{x2}$ provided by sensor arrangement 60.

The use of the sensor signals $x_{s1}$, $x_{x2}$ for measuring the viscosity η is based on the surprising recognition that the velocity θ of the motion of the fluid, which causes the viscous friction, has, at least in the operating range of transducer assemblies of the kind described, a reproducible relationship, particularly a linear relationship, to the instantaneous lateral deflection of flow tube 13. Thus, it can be assumed with a good approximation that $$X_\theta = K_1 \cdot X_v \qquad (1)$$

where $X_v$ = a velocity value derived from sensor signal $x_{s1}$ and/or from sensor signal $x_{s2}$ and representative of an instantaneous velocity of the lateral deflection of flow tube 13

$X_\theta$ = an estimate of the velocity θ of the motion of the fluid, which causes shear forces and, thus, viscous friction in the fluid $K_1$ = a proportionality factor to be determined, particularly by calibration measurements.

The velocity value $X_v$ may be a signal value, e.g., an instantaneous signal amplitude, derived either from a single sensor signal $x_{s1}$, $x_{s2}$ or from both sensor signals $x_{s1}$, $x_{s2}$, particularly from the sum of the latter, $x_{s1}+x_{s2}$. If sensors 17, 18 are arranged symmetrically with respect to the midpoint of flow tube 13, and the sensor signals $x_{s1}$, $x_{s2}$, as mentioned, have the same amplitude or an amplitude regulated at the same value, the signal sum $x_{s1}+x_{s2}$ in transducer assembly 10 of the embodiment is proportional to the lateral deflection at the midpoint of flow tube 13.

Figure 5:
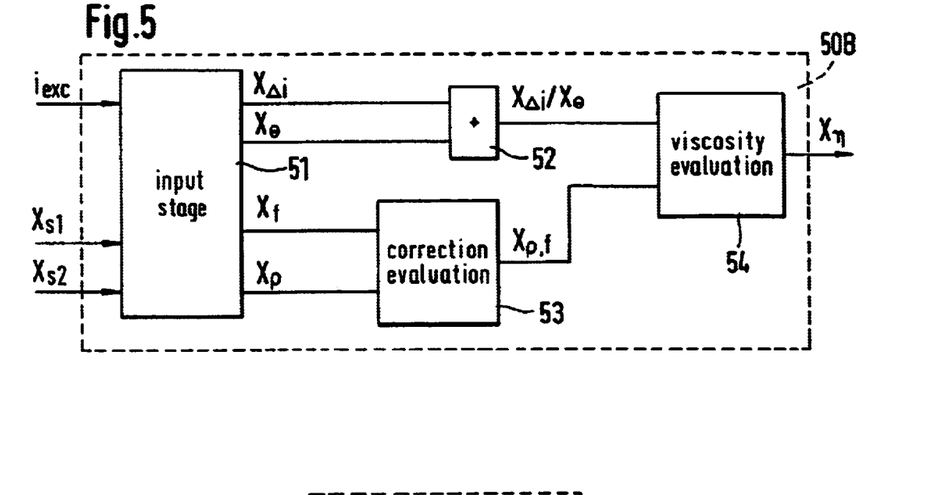
FIG. 5 is a schematic block diagram of an evaluating circuit of a vibration meter as shown in FIG. 1.
Figure 6:
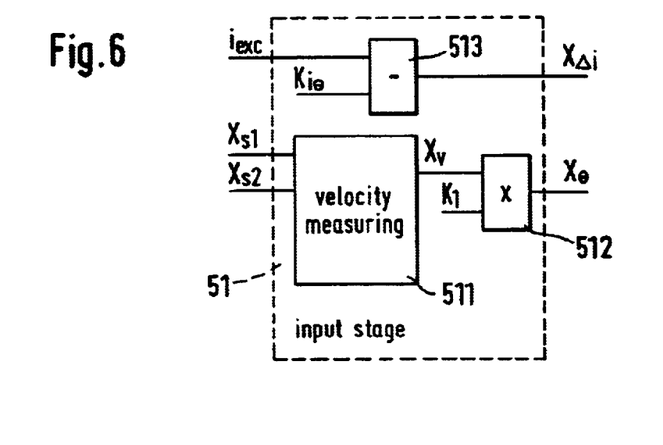
FIGS. 6 to 9 are schematic block diagrams of embodiments of the evaluating circuit of FIG. 5.

To generate the estimate $X_\theta$ of the velocity θ, the evaluating circuit 50B, as shown in FIGS. 5 and 6, comprises an input stage 51 with a velocity or first measuring circuit 511, which processes the sensor signal $x_{s1}$ and/or the sensor signal $x_{s2}$ to generate the velocity value $X_v$. Such a measuring circuit, particularly a circuit measuring signal amplitudes, is shown, for example, in U.S. Pat. No. 5,648,616 or European Patent 866 319, the disclosers of which are hereby incorporated by reference.

As shown schematically in FIG. 6, this input stage 51 further comprises a multiplier 512, which serves to implement Equation (1), i.e., which multiplies the velocity value $X_v$, provided by measuring circuit 511 and presented to a first input, by a velocity proportionality factor $K_1$, presented to a second input, and thus produces as output the estimate $X_\theta$.

The relationship formulated by Equation (1) may be determined for respective concrete realizations of transducer assembly 10 by suitable calibration measurements, and implemented in meter electronics 50. To determine the proportionality factor $K_1$, for example, the actual velocity of the torsion at the midpoint of flow tube 13 may be determined during a calibration measurement and related to the simultaneously generated sensor signals $x_{s1}$ and/or $x_{s2}$. It is also possible to calculate the proportionality factor $K_1$ for a series of transducers numerically, for example by using finite-element methods familiar to those skilled in the art.

Particularly if the fluid to be measured is a non-Newtonian fluid, the effect of the instantaneous mass flow rate on the velocity θ, and thus on the determination of the estimate $X_\theta$, may be taken into account. In a non-Newtonian fluid, the shear forces would decrease with increasing mass flow rate m.

To calibrate the transducer assembly 10, two or more different fluids with known parameters, such as density ρ, mass flow rate m, viscosity η, and/or temperature, are passed one after the other through transducer assembly 10, and the responses of transducer assembly 10, such as the instantaneous excitation current $i_{exc}$ and/or the instantaneous excitation frequency $f_{exc}$, are measured. The set parameters and the respective measured responses of transducer assembly 10 are related to each other, and thus mapped onto the corresponding calibration constants, such as the proportionality factor $K_1$. The calibration constants determined can then be stored in the form of digital data in a table memory of evaluating circuit 50B; however, they can also be used as analog settings for suitable arithmetic circuits. At this point it should be noted that the calibration of transducers is familiar to those skilled in the art and therefore need not be explained in greater detail.

The damping of the vibrations of flow tube 13, besides being determined by the damping component due to viscous friction, is also determined by a damping component that is virtually independent of the fluid. This damping component is caused by friction forces that act in excitation arrangement 16 and in the material of flow tube 13, for example. In other words, the measured excitation current $i_{exc}$ represents the entirety of the friction forces and/or friction torques in transducer assembly 10. Accordingly, to determine the viscosity η of the fluid, the fluid-independent damping component may be eliminated from the ratio $i_{exc}/θ$, i.e., a ratio $Δi_{exc}/θ$ of an excitation current component $Δi_{exc}$, which corresponds to the damping component of the excitation current $i_{exc}$ that is due to viscous friction, to the velocity θ may be determined.

To obtain a friction value $X_{Ai}$ representative of the excitation current component 66 $i_{exc}$ and thus of the viscous friction, during operation of the vibration meter, a no-load-current value $K_{i0}$, which represents the aforementioned friction forces in excitation arrangement 16, is subtracted in input stage 51 from the excitation current $i_{exc}$ or from a measured value representing the instantaneous excitation current. To accomplish this, input stage 51, as shown schematically in FIG. 6, comprises a second measuring circuit 513, particularly a digitizing measuring circuit, which subtracts the no-load current value $K_{i0}$ applied at a subtrahend input from the excitation current $i_{exc}$ or the measured excitation current value applied at a minuend input and thus produces as output the friction value $X_{Ai}$.

The no-load current value $K_{i0}$, too, may be determined during a calibration of the vibration meter, e.g. for an evacuated or only air-conducting flow tube 13, and stored or set in meter electronics 50. It is readily apparent to those skilled in the art that if necessary, other physical parameters influencing the no-load current value $K_{i0}$, such as an instantaneous temperature of the flow tube and/or the fluid, may be taken into account in calibrating the no-load current value $K_{i0}$.

To generate a corresponding quotient value $X_{Ai}/X_\theta$ for the damping component $Δi_{exc}/θ$, which is due to viscous friction in the fluid, evaluating circuit 50B, as shown in FIG. 5, further comprises a first function block 52, which serves to divide the measured friction value $X_{Ai}$, applied at a dividend input, by the estimate $X_\theta$, applied at a divisor input.

In determining the viscosity η by a transducer assembly of the kind described, besides the excitation current $i_{exc}$ and the velocity θ, a frequency of the vibrations of flow tube 13 as well as the density ρ of the fluid may be taken into account, cf. U.S. Pat. No. 4,524,610 .

To that end, the evaluating circuit 50B further comprises a correction evaluating or second function block 53, which serves to derive from the measured density value $X_\rho$ and the measured excitation frequency value $X_f$ a corresponding correction value $X_{\rho,f}$, which is dependent on the density $\rho$ of the fluid and on the excitation frequency $f_{exc}$.

Both the density value $X_\rho$ and the excitation frequency value $X_f$ are values which are commonly measured during operation of vibration meters of the kind described, particularly of Coriolis mass flowmeter-densimeters, cf., for example, U.S. Pat. Nos. 4,187,721, 4,524,610, 4,876,879, 5,648,616, or 5,687,100, or European Patent 866 319, the disclosers of which are hereby incorporated by reference. Thus it can be assumed that these measured values $X_f$, $X_\rho$ are available for determining the viscosity $\eta$ in accordance with the invention.

For the correction value $X_{\rho,f}$, particularly with flow tube 13 torsionally vibrating in the manner described, the following relationship, which is implemented with function block 53, is true with a good approximation:

$$X_{\rho,f} = X_\rho \cdot X_f \quad (2)$$

If displacement sensors are used for sensors 17, 18, instead of the simple excitation frequency value $X_f$, the square $X_f^2$ of this value is used to determine the correction value $X_{\rho,f}$, i.e., besides a multiplier for Equation (2), function block 53 may contain a further multiplier or a squarer.

As shown in FIG. 5, both the quotient value $X_{\Delta i}/X_\theta$ and the correction value $X_{\rho,f}$ are supplied to a viscosity or third function block 54 of evaluating circuit 50B, which derives the viscosity value $X_\eta$ from these values.

In a preferred embodiment of the invention, the determination of the viscosity $\eta$ is based on the following relationship:

$$X_\eta = \frac{K_2}{X_{\rho,f}} \cdot \left(\frac{X_{\Delta i}}{X_\theta}\right)^2 \quad (3)$$

where $K_2$ is a constant to be determined by calibration, particularly a constant dependent on the square of the nominal diameter of flow tube 13.

It has turned out that the lower the viscosity $\eta$ and/or the higher the density $\rho$ of the fluid, the more closely the viscosity value $X_\eta$ determined according to Eq. (3) will conform to the actual viscosity $\eta$. Furthermore, the greater the nominal diameter of flow tube 13, the more accurately the viscosity $\eta$ will be determined in this embodiment of the invention.

Therefore, in a further preferred embodiment of the method of the invention, a more accurate determination of the viscosity value $X_\eta$, particularly at a viscosity $\rho$ greater than 5 Pas (=pascal seconds) and/or at nominal flow tube diameters less than 8 mm (=millimeters), is based on the following relationship:

$$X_\eta = \frac{1}{2} \cdot K_2 \cdot K_3 \cdot K_4 \cdot X_{\rho,f} \cdot \left(1 - \sqrt{1 - \frac{K_4}{K_3 \cdot X_{\rho,f}} \cdot \frac{X_{\Delta i}}{X_\theta}}\right)^2 \quad (4)$$

where
 $K_3$=a calculated constant and
 $K_4$=a constant to be determined by calibration.

Equation (4) represents a universal solution for transducers whose flow tube or flow tubes are excited into torsional vibrations about a longitudinal flow tube axis. For the transducer assembly 10 of the embodiment, a value of constant $K_3$ lies in a range of about 0.24 to 0.25, for example. Equation (4) takes account of the fact that within the operating range of transducers of the kind described, particularly of transducers with a flow tube performing torsional vibrations as described, the effect of the viscosity-dependent friction forces acting in the fluid on the excitation current component $_\Delta i_{exc}$ decreases in a radial direction toward the longitudinal flow tube axis. The constant $K_3$ is a coefficient for a quadratic part of the aforementioned decrease. If the excitation current component $_\Delta i_{exc}$, and thus the friction value $X_{\Delta 1}$, tends to very small values, Equation (4) will change to Equation (3).

Figure 7:
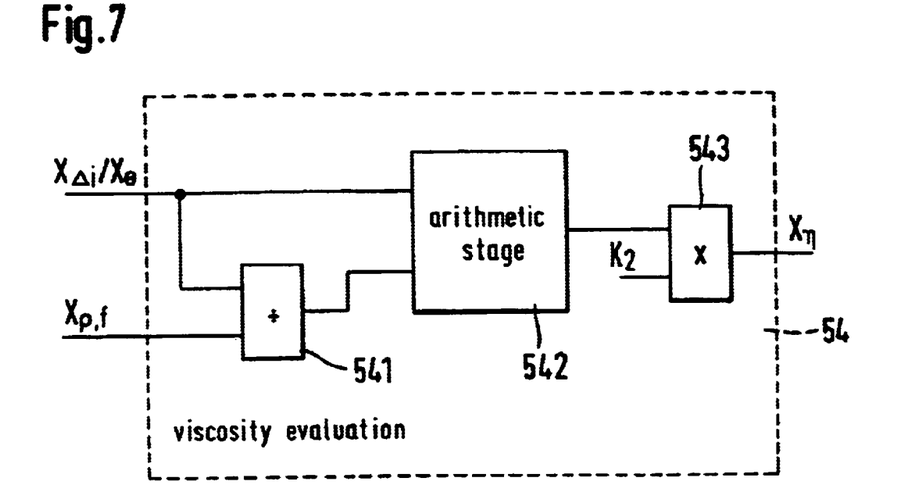
Figure 8:
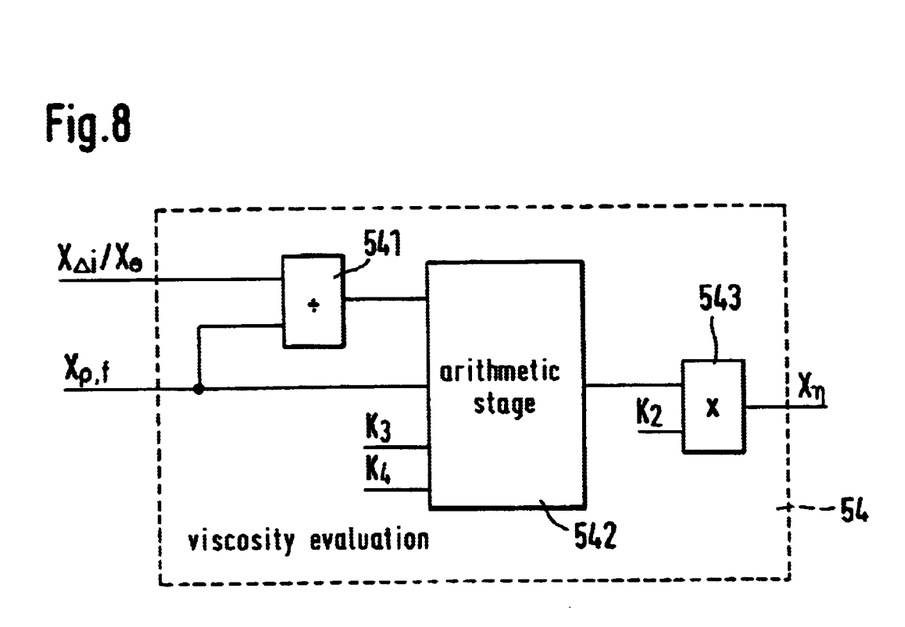

To implement Equations (3) and (4), function block 54, in preferred embodiments of the invention shown in FIGS. 7 and 8, respectively, comprises a divider 541 with a dividend input for the quotient value $X_{\Delta i}/X_\theta$ and a divisor input for the correction value $X_{\rho,f}$ to produce a first intermediate value. Function block 54 further comprises an arithmetic stage 542 with a first input for the first intermediate value to produce a second intermediate value proportional to the viscosity $\eta$, and a multiplier 543, which multiplies the second intermediate value by the constant $K_2$ to obtain the viscosity value $X_\eta$.

To implement Equation (3), arithmetic stage 542, in another preferred embodiment of the invention, is configured as a multiplier which, as shown schematically in FIG. 7, serves to multiply the first intermediate value, provided by divider 541, by the quotient value $X_{\Delta 1}/X_\theta$ to produce the second intermediate value.

To implement Equation (4), arithmetic stage 542, in a further preferred embodiment of the invention, comprises a square-root extractor for the difference under the radical sign of Equation (4) and a squarer for the difference with the radical sign. Arithmetic stage 542 further serves to multiply a square value generated by the squarer by the constants $K_3$ and $K_4$ and by the correction value $X_{\rho,f}$ to produce the second intermediate value.

It has also turned out that the above-described estimate of the velocity $\theta$ according to Eq. (1) also depends to a slight degree on the density $\rho$ of the fluid, so that $$K_1 = K_1(\rho) \quad (5)$$

Investigations have shown that for the transducer assembly 10 of the embodiment, the proportionality factor $K_1$, taking account of its density dependence, may be determined from:

$$K_1 = \frac{K_{1,0}}{1 + K_5 \cdot (X_\rho - \rho_0)} \quad (6)$$

where
 $\rho_0$=a set or measured density of a calibration fluid serving to calibrate transducer assembly 10;
 $K_{1,0}$=a proportionality factor for the transducer assembly 10 conducting the calibration fluid; and
 $K_5$=a constant to be calibrated, which is dependent on the nominal diameter of flow tube 13.

In analogy to Eq. (1), the proportionality factor $K_{1,0}$ is given by $$K_{1,0} = \frac{X_{\theta,0}}{X_{v,0}} \quad (7)$$

where
 $X_{\theta,0}$=a first measured calibration value, representative of the velocity $\theta$ for the flow tube 13 conducting the calibration fluid; and $X_{v,0}$ = a second measured calibration value, derived from sensor signal $x_{s1}$ and/or sensor signal $x_{s2}$ and representative of a velocity of the lateral deflection of the flow tube 13 conducting the calibration fluid.

Figure 9:
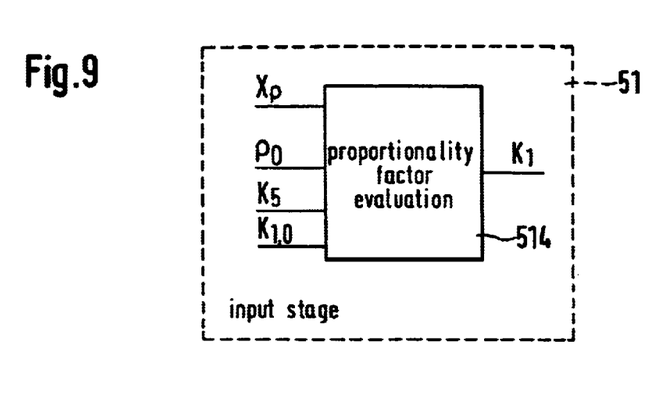

Equation (6), as shown schematically in FIG. 9, is implemented with a proportionality factor function block 514 of input stage 51.

The aforementioned function blocks 52, 53, 54, 514 and the multiplier 512,which serve to produce the viscosity value $X_\rho$, may be implemented in the manner familiar to those skilled in the art using, for instance, a microcomputer provided in evaluating circuit 50B and suitable program codes that are implemented and executed in this microcomputer. The implementation of the above Equations (1), (2), (3), (4), and (6) in the respective function blocks as well as the creation of microcomputer program codes serving to implement Equations (1), (2), (3), (4), and (6) are familiar to those skilled in the art and can thus be carried out without more detailed explanations. Of course, the equations can also be represented, in whole or in part, using suitable discrete-component, analog and/or arithmetic circuits in evaluating circuit 50B. In a corresponding manner, input stage 51 can be implemented with the aforementioned microcomputer, in which case the sensor signals $x_{s1}$, $x_{s2}$ and the sensed excitation current $i_{exc}$ may, of course, be converted into corresponding digital signals using analog-to-digital converters, cf. particularly European Patent 866 319.

In the transducer assembly 10 of the embodiment, because of the torsion in particular, a ratio $_\Delta i_{exc}/i_{exc}$ of the excitation current component $_\Delta i_{exc}$ to the excitation current $i_{exc}$, normalized to a reference viscosity of about 4 Pas, can be up to 90%, i.e., transducer assembly 10 exhibits a very high sensitivity to the viscosity η.

It is also possible to use other transducers familiar to those skilled in the art, such as transducers with a helically bent flow tube, as are described, for example, in U.S. Pat. Nos. 5,357,811, or 5,557,973 for measuring the viscosity $_\eta$. Also, as mentioned above, transducers with straight or bent flow tubes as are described, for example, in U.S. Pat. 5,301,557, 5,648,616 or 5,796,011, can be used for measuring the viscosity η. Such transducers may, for instance, have a ratio $_\Delta i_{exc}/i_{exc}$, related to the aforementioned reference viscosity, of approximately 70% to 80%.

While the invention has been illustrated and described in detail in the drawings and forgoing description, such illustration and description is to be considered as exemplary not restrictive in character, it being understood that only exemplary embodiments have been shown and described and that all changes and modifications that come within the spirit and scope of the invention as described herein are desired to protected.

What is claimed is:

1. A method of measuring a viscosity of a fluid flowing through a pipe, using a vibration meter comprising:
    a transducer assembly
        with at least one flow tube inserted into the pipe which in operation oscillates relative to a position of rest at an adjustable excitation frequency,
        with an electromechanical excitation arrangement for producing spatial deflections of the flow tube, and
        with a sensor arrangement, responsive to lateral deflections of the flow tube, for sensing an inlet-side and an outlet-side deflection of the flow tube; and
    meter electronics with
        an excitation circuit which generates an excitation current feeding the excitation arrangement, and
        an evaluating circuit,
    the vibration meter providing a density value, representative of a density of the fluid, and an excitation frequency value, representative of the excitation frequency,
said method comprising the steps of:
    generating vibrations of the flow tube at the excitation frequency to produce viscous friction in the fluid;
    sensing the excitation current feeding the excitation arrangement to generate a friction value representative of the viscous friction;
    sensing an inlet-side and/or an outlet-side deflection of the flow tube to generate an estimate representative of a velocity of a motion of the fluid, which causes the viscous friction;
    dividing the friction value by the estimate to obtain a quotient value representative of a damping of the oscillating flow tube caused by the viscous friction;
    deriving from the density value and the excitation frequency value a correction value dependent on the density of the fluid and on the excitation frequency; and
    deriving from the quotient value and the correction value a viscosity value representative of the viscosity of the fluid.

2. A method as claimed in claim 1 wherein the viscosity value is obtained by dividing the quotient value by the correction value.

3. A method as claimed in claim 1 wherein the viscosity value is obtained by squaring the quotient value.

4. A vibration meter for measuring a viscosity of a fluid flowing through a pipe, which vibration meter comprises:
    a transducer assembly including at least one flow tube being inserted into the pipe, said flow tube having a lumen conducting the fluid and said flow tube being clamped at an inlet end and an outlet end so as to be capable of vibrating, an electromechanical excitation arrangement driving said flow tube to oscillate in a bending mode at least partially for producing viscous friction within the fluid, and a sensor arrangement, responsive to oscillations of the flow tube, for generating at least one sensor signal, representative of lateral deflections of the flow tube; and
    meter electronics including an excitation circuit which generates an excitation current feeding the excitation arrangement, and an evaluating circuit which derives from said at least one sensor signal and from the excitation current a viscosity value representative of the viscosity of the fluid, wherein the evaluating circuit also uses a density value representative of a density of the fluid for determining the viscosity value.

5. The vibration meter as claimed in claim 4, wherein the evaluating circuit derives the density value from the at least one sensor signal.

6. A vibration meter for measuring a viscosity of a fluid flowing through a pipe, which vibration meter comprises:
    a transducer assembly including at least one flow tube being inserted into the pipe, said flow tube having a lumen conducting the fluid and said flow tube being clamped at an inlet end and an outlet end so as to be capable of vibrating, an electromechanical excitation arrangement driving said flow tube to oscillate in a bending mode at least partially for producing viscous friction within the fluid, and a sensor arrangement, responsive to oscillations of the flow tube, for generating at least one sensor signal, representative of lateral deflections of the flow tube; and meter electronics including an excitation circuit which generates an excitation current feeding the excitation arrangement, and an evaluating circuit which derives from said at least one sensor signal and from the excitation current a viscosity value representative of the viscosity of the fluid, wherein the evaluating circuit estimates a velocity of a motion of the fluid, said motion causing a viscous friction within said fluid, the evaluating circuit uses the at least one sensor signal for estimating said velocity, and the evaluating circuit determines the viscosity value depending on said motion being estimated.

7. A method of measuring a viscosity of a fluid flowing through a pipe, said method comprising the steps of:

using an electromechanical excitation arrangement for driving a flow tube being inserted into the pipe and conducting said fluid;

feeding said excitation arrangement by an oscillating excitation current and driving said flow tube to vibrate in a bending mode at least partially, said bending mode vibrations causing lateral deflections of said flow tube and said bending mode vibrations producing viscous friction within said fluid;

sensing oscillations of said flow tube by using a sensor arrangement being responsive to lateral oscillations of the flow tube and generating at least one sensor signal being representative of lateral oscillations of the flow tube;

deriving from said at least one sensor signal and from said excitation current a viscosity value representative of the viscosity of the fluid, wherein the step of deriving the viscosity value further comprises the steps of: determining a density of the fluid for generating a density value being representative of said density of the fluid; and using said density value for determining said viscosity to be measured.

8. The method meter as claimed in claim 7, wherein the step of determining the density of the fluid comprises the step of deriving the density value from said at least one sensor signal.

9. A method of measuring a viscosity of a fluid flowing through a pipe, said method comprising the steps of:

using an electromechanical excitation arrangement for driving a flow tube being inserted into the pipe and conducting said fluid;

feeding said excitation arrangement by an oscillating excitation current and driving said flow tube to vibrate in a bending mode at least partially, said bending mode vibrations causing lateral deflections of said flow tube and said bending mode vibrations producing viscous friction within said fluid;

sensing oscillations of said flow tube by using a sensor arrangement being responsive to lateral oscillations of the flow tube and generating at least one sensor signal being representative of lateral oscillations of the flow tube; and deriving from said at least one sensor signal and from said excitation current a viscosity value representative of the viscosity of the fluid, wherein the excitation current has an excitation frequency corresponding to a mechanical resonance frequency of the flow tube, and the step of deriving the viscosity value comprises the step of deriving from the density value a correction value depending on the density of the fluid and the excitation frequency.

10. The method meter as claimed in claim 9, wherein the step of deriving the viscosity value comprises the step correcting the determined damping of deflections of the flow tube by using the correction value.

11. The method meter as claimed in claim 9, wherein the step of deriving the viscosity value comprises the step correcting the determined damping of deflections of the flow tube by using the correction value.

12. A method of measuring a viscosity of a fluid flowing through a pipe, said method comprising the steps of:

using an electromechanical excitation arrangement for driving a flow tube being inserted into the pipe and conducting said fluid;

feeding said excitation arrangement by an oscillating excitation current and driving said flow tube to vibrate in a bending mode at least partially, said bending mode vibrations causing lateral deflections of said flow tube and said bending mode vibrations producing viscous friction within said fluid;

sensing oscillations of said flow tube by using a sensor arrangement being responsive to lateral oscillations of the flow tube and generating at least one sensor signal being representative of lateral oscillations of the flow tube; and deriving from said at least one sensor signal and from said excitation current a viscosity value representative of the viscosity of the fluid, wherein the excitation current has an excitation frequency corresponding to a mechanical resonance frequency of the flow tube, the step of deriving the viscosity value comprises the step of generating an excitation frequency value representative of said excitation frequency, and the step of deriving the viscosity value comprises the step of deriving from the excitation frequency value a correction value depending on the density of the fluid and the excitation frequency.

* * * * *